United States Patent [19]

Wu

[11] 4,338,095
[45] * Jul. 6, 1982

[54] METHOD FOR SELECTIVE DETERMINATION OF CONJUGATED AND UNCONJUGATED BILIRUBIN

[75] Inventor: Tai-Wing Wu, Rochester, N.Y.

[73] Assignee: Eastman Kodak Company, Rochester, N.Y.

[*] Notice: The portion of the term of this patent subsequent to Jan. 19, 1999, has been disclaimed.

[21] Appl. No.: 167,999

[22] Filed: Jul. 14, 1980

Related U.S. Application Data

[63] Continuation-in-part of Ser. No. 56,584, Jul. 11, 1980, abandoned.

[51] Int. Cl.³ ............................................. G01N 33/72
[52] U.S. Cl. ................................... 23/230 B; 23/905; 422/56
[58] Field of Search ............................. 23/230 B, 905; 422/55–57; 260/112 R, 112 B

[56] References Cited

U.S. PATENT DOCUMENTS 4,069,017  1/1978  Wu et al. ............................. 23/230 B
4,204,839  5/1980  Wu et al. ............................. 23/230 B

OTHER PUBLICATIONS

Ostrow et al., "Isolation and Properties of Conjugated Bilirubin from Bile", Biochem. J. (1970) 120, 311–327.

Primary Examiner—Arnold Turk
Attorney, Agent, or Firm—J. Jeffrey Hawley

[57] ABSTRACT

A method is described for the selective determination of the conjugated bilirubin ($B_c$) or unconjugated bilirubin ($B_u$), as well as the total bilirubin ($B_T$), content of an aqueous liquid. The method comprises contacting the aqueous liquid with an analytical element having a dry reagent zone comprising an interactive mordant for bilirubin and thereafter detecting the absorption or emission spectra of the aqueous liquid at two or more wavelengths. The respective molar absorption or emission characteristics of $B_u$ and $B_c$ are predetermined for at least two of these wavelengths using a molecular weight of 584 for $B_u$ and a molecular weight in the range from about 750 to about 940 for $B_c$. The $B_u$, $B_c$ and/or $B_T$ content is determined from such spectra and absorption or emission characteristics. The interactive mordant for bilirubin is used to enhance the absorption characteristics or produce fluorescent emission of mordanted bilirubin.

13 Claims, 2 Drawing Figures

METHOD FOR SELECTIVE DETERMINATION OF CONJUGATED AND UNCONJUGATED BILIRUBIN

This is a Continuation-in-Part of U.S. patent application Ser. No. 056,584, filed July 11, 1980, now abandoned.

FIELD OF THE INVENTION

The present invention relates to a method for selectively determining the presence of conjugated and unconjugated bilirubin components, as well as the total bilirubin content, of an aqueous liquid containing these bilirubin components.

BACKGROUND OF THE INVENTION

Bilirubin is a degradation product of hemoglobin. It has been estimated that approximately 200–230 milligrams of bilirubin and its derivatives are formed each day in the normal human adult by the degradation of hemoglobin within the liver, spleen, and bone marrow.

In human body fluids such as bile and serum, bilirubin exists in two different forms, these forms commonly being referred to in the clinical literature as conjugated bilirubin, $B_c$, and unconjugated bilirubin, $B_u$. The total bilirubin content $B_T$ represents the sum of $B_u$ and $B_c$.

Unconjugated bilirubin has a well-established molecular structure and constitutes the predominant portion of the total bilirubin content. For example, in normal human adult serum $B_u$ constitutes about 80 percent by weight of the total bilirubin content thereof. The molecular weight of $B_u$ is 584 and its molecular structure is as follows:

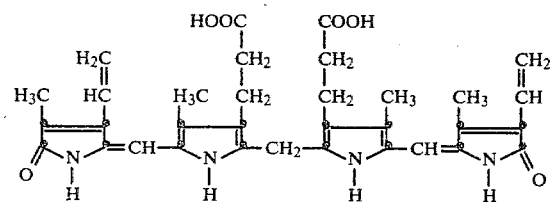

$B_c$, believed to represent about 1 to 20 wt percent of the total bilirubin present in normal adult serum, is unstable in pure form and extremely difficult to isolate. Extensive study and reseach effort has been conducted to isolate this bilirubin component and to determine its molecular structure.

$B_c$ has traditionally been considered to represent the reaction product of $B_u$ esterified with sugar groups. However, owing to its instability, the specific molecular structure of any conjugated form of bilirubin had not been established until quite recently when a diconjugate $B_c$ species was separated from human bile and, for the first time, the molecular structure of a $B_c$ species was determined by the present inventor with the aid of coworkers. See paper entitled "Human Conjugated Bilirubin—Isolation, Biosynthesis And Molecular Characterization By Direct Spectroscopic Analyses", T. W. Wu et al., presented at the Americal Association for Clinical Chemistry 31st Annual Meeting in New Orleans, Louisiana, July 15–20, 1979. An abstract of this paper appears in Clinical Chemistry, Vol. 25, No. 6, p. 1137, June, 1979. Even more recently, the present inventor has isolated and identified small amounts of a substance having this same molecular structure in human serum. This diconjugate form of bilirubin has now been identified in both bile and serum. It was first determined to have a molecular structure as follows:

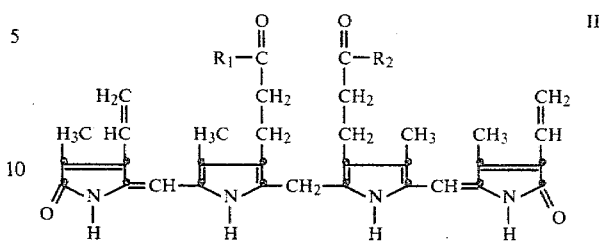

where $R_1$ = glucuronic acid and $R_2$ = glucuronolactone or $R_1$ = glucuronolactone and $R_2$ = glucuronic acid and since has been determined also to have a related diconjugate structure wherein both $R_1$ and $R_2$ are glucuronic acid. A monoconjugate species also exists wherein $R_1$ is glucuronic acid or glucuronolactone and $R_2$ is —OH. These mono- and diconjugate species coexist in any given body fluid sample and are, essentially, as far as can be ascertained, spectrally indistinguishable. Accordingly, a molecular weight assignable to $B_c$ falls within the range from about 750 to about 940. The singular term $B_c$, therefore, as used herein represents a composite of $B_c$ species having a molecular weight in the above defined range.

The diagnostic significance of bilirubin is well established. For example, an excessive amount of bilirubin within the human body, referred to as jaundice, is recognized as evidence of a variety of disease conditions, particularly diseases of the liver. In addition, in certain pathological conditions, for example, obstructive jaundice, the small amount of $B_c$ normally present in adult human serum becomes elevated to form a larger proportion of the total bilirubin content. Thus, to facilitate early diagnosis of certain disease states, a bilirubin analysis that selectively determines the presence and/or concentration of both $B_c$ and $B_u$, as well as the total bilirubin content of human serum, would be highly useful.

Prior to the present invention, to the knowledge of the inventor, no radiometric assay (i.e., no assay based on detection of spectral absorption or emission) was available for the selective determination of $B_c$ and $B_u$. Various assays are available which provide so-called "direct" and "indirect", as well as "total" bilirubin values. Some authors have claimed that "direct" bilirubin values can be equated with $B_c$, while the "indirect" values correspond to $B_u$. However, as observed by Henry, Cannon, and Winkelman in Clinical Chemistry, Principles And Technics, Harper and Row, p. 1045 (1974), "direct" bilirubin samples have been found to include $B_c$ components, such as bilirubin diglucuronide, as well as $B_u$. Thus, one cannot simply equate "direct" or "indirect" bilirubin values with either the conjugated or unconjugated bilirubin components of a biological liquid.

Furthermore, some believe that "direct" and "indirect" bilirubin have the same absorption spectra in serum. See Henry et al. referenced above at pp. 1071 and 1072. Based on this view, one would not expect that the different forms of bilirubin could be spectrophotometrically differentiated in a radiometric assay.

Prior to the present invention, radiometric assays for bilirubin, such as colorimetric and fluorimetric assays, measured an absorption or emission spectrum of bilirubin or a bilirubin reaction product and determined final bilirubin concentration values essentially on the basis that the total bilirubin present in an unknown sample was predominantly in the form of $B_u$. For example, a colorimetric assay can be conducted by (i) detecting the absorbance, A, of an unknown bilirubin-containing sample; (ii) applying Beer's Law:

$$A = \epsilon \cdot C \cdot L \qquad \text{III}$$

where
A represents absorbance,
$\epsilon$ represents molar absorptivity of bilirubin or a bilirubin reaction product
C represents bilirubin concentration in moles/liter, and
L represents pathlength;
and (iii) comparing the detected value of A to a calibration curve based on known amounts of $B_u$; whereby the molar concentration, C, of bilirubin in an unknown sample can be determined. The resultant molar concentration, C, is then converted to an absolute amount, such as mg/dl, using the molecular weight of $B_u$.

These radiometric assays for bilirubin fail to account for the presence of $B_c$ and essentially ignore its contribution to the absorption and/or emission spectra of an unknown bilirubin-containing sample. To the extent that normal adult serum is composed predominantly of $B_u$, the foregoing failure poses no real problem. However, in those cases where the concentration of $B_c$ is elevated so that it represents a larger than normal proportion of the total bilirubin content, the foregoing failure of known radiometric assays for bilirubin leads to serious assay error. Moreover, prior to the present invention, in the absence of molecular weight and spectral absorption and/or emission data on $B_c$, the foregoing radiometric assay errors were difficult, if not impossible, to prevent.

Recently, Wu et al U.S. Pat. No. 4,069,017 issued Jan. 17, 1978, and Wu et al U.S. Ser. No. 932,158 filed Aug. 9, 1978, now U.S. Pat. No. 4,204,839, have described a new colorimetric and a new fluorimetric assay, respectively, for the determination of bilirubin. These new assays employ interactive mordants for bilirubin.

The mordanted bilirubin, as described in U.S. Pat. No. 4,069,017, facilitates the colorimetric detection of bilirubin in an aqueous liquid sample owing to the marked increase in the molar extinction coefficient exhibited by the mordanted bilirubin compared to that of free bilirubin and by the shift in absorption peak of the mordanted bilirubin compared to that exhibited by free bilirubin admixed in an aqueous liquid. The mordanted bilirubin, as described in U.S. Ser. No. 932,158, has also been found to exhibit fluorescence and therefore one can also determine the presence and/or concentration of bilirubin fluorimetrically by use of the mordanted bilirubin. Neither U.S. Ser. No. '158 nor U.S. Pat. No. '017, however, disclose how the mordant interacts with $B_u$ and $B_c$ individually.

SUMMARY OF THE INVENTION

The present invention features a radiometric method for the selective determination of unconjugated bilirubin ($B_u$) or conjugated bilirubin ($B_c$) as well as the total bilirubin ($B_T$) content of an aqueous liquid. The method comprises contacting together an analytical element having an essentially dry reagent zone comprising an interactive mordant for bilirubin with an aqueous liquid containing $B_u$ and $B_c$ to produce mordanted $B_c$ and $B_u$.

The mordanted $B_c$ and $B_u$ components exhibit a detectable absorption or emission spectrum containing individual absorption or emission bands characteristic of each of the bilirubin components in the liquid. The method further comprises detecting the absorption or emission spectra of the mordanted bilirubin at two or more wavelengths, one wavelength being at or near an absorption or emission maximum of mordanted $B_u$, and the other being at or near an absorption or emission maximum of mordanted $B_c$. The respective molar absorption or emission characteristics of both mordanted $B_u$ and mordanted $B_c$ are predetermined, as set forth in greater detail hereinafter, for at least two of these wavelengths based on a molecular weight for $B_u$ of 584 and a molecular weight for $B_c$ in the range from about 750 to about 940. Thereafter, $B_u$, $B_c$ or $B_T$ are determined from the detected spectra and the $B_u$ and $B_c$ molar absorption or emission characteristics.

The method of the invention can be carried out using either absorption photometry, e.g., colorimetric detection, or emission photometry, e.g., fluorimetric detection, as an appropriate mode of radiometric detection.

In the present method the interactive mordant for bilirubin, upon mordanting $B_c$ and $B_u$, enhances the molar absorptivities of $B_u$ and $B_c$, shifts the absorption maximum of $B_u$, and produces fluorescence emission of $B_u$ and $B_c$, thereby permitting the selective radiometric detection of both $B_u$ and $B_c$. A preferred interactive mordant comprises binding sites for bilirubin and at least one moiety having a hydrophobic organic matrix containing a charge-bearing cationic group. In those embodiments of the invention which employ an absorption detection mode, the mordanted $B_c$ and mordanted $B_u$ exhibit an increase in their molar extinction coefficient compared to those exhibited by unmordanted $B_u$ and $B_c$. In those embodiments which employ an emission detection mode, each of the mordanted $B_u$ and $B_c$, upon being subjected to activating radiation effective to excite the mordanted $B_c$ or $B_u$, exhibit a characteristic detectable fluorescence emission at a wavelength at which neither the unmordanted bilirubin components (i.e., $B_c$ and $B_u$), nor the interactive mordant, otherwise exhibits detectable fluorescence.

The assay method of the invention can advantageously provide several different bilirubin assay values. For example, this method can directly determine the presence and/or concentration of $B_u$, or the presence and/or concentration of $B_c$ employing a $B_c$ molecular weight in the range from about 750 to about 940. In addition, by adding together the amounts of these two different bilirubin components, one can also obtain a highly quantitative $B_T$ assay value. Thus, by interacting a single sample of the aqueous liquid to be assayed with a single amount of the interactive mordant, one can conveniently obtain a quantitative determination of $B_u$, $B_c$, and $B_T$.

The method of the invention is carried out using "dry chemistry" analytical techniques. "Dry chemistry" refers to analytical chemical techniques wherein the assay reagent(s) is contained in dry test element prepared, for example, by imbibing, impregnating, or coating the reagent(s) to form an essentially dry reagent zone. Dry chemistry test elements include "dip-and-read" fibrous test strips or non-fibrous, multi-zone test elements such as the multilayer test elements described in Pryzbylowicz and Millikan, U.S. Pat. No. 3,992,158 issued Nov. 16, 1976 and the above-referenced Wu et al U.S. Pat. No. 4,069,017.

In an especially preferred embodiment, the dry chemistry analytical element is a multi-zone element comprising a reagent zone as described above and a spreading zone that can effectively distribute and meter the aqueous test sample to the reagent zone. In this embodiment, such multi-zone elements can be integral elements wherein the spreading zone and reagent zone are superposed layers in fluid contact with one another under conditions of use. Optionally, these layers can be carried on a suitable support, such as a "radiation-transmissive" support.

The term "radiation-transmissive" refers to zones, supports, and other layers of an element that permit effective passage of electromagnetic radiation used to detect an analytical result produced in the element. Typically, such "radiation-transmissive" zones, supports, and other layers are transmissive of radiation having a wavelength within the region of from about 200 to about 800 nm, preferably from about 300 nm to about 700 nm.

DESCRIPTION OF THE PREFERRED EMBODIMENTS

The present radiometric assay method for $B_c$, $B_u$, and, if desired, $B_T$ has heretofore not been possible because of the general lack of information regarding any specific molecular structure of $B_c$ and its molar absorption or emission characteristics, e.g., its absorption spectrum and its molar extinction coefficient, $\epsilon$, (sometimes referred to as molar absorptivity).

Figure 1:
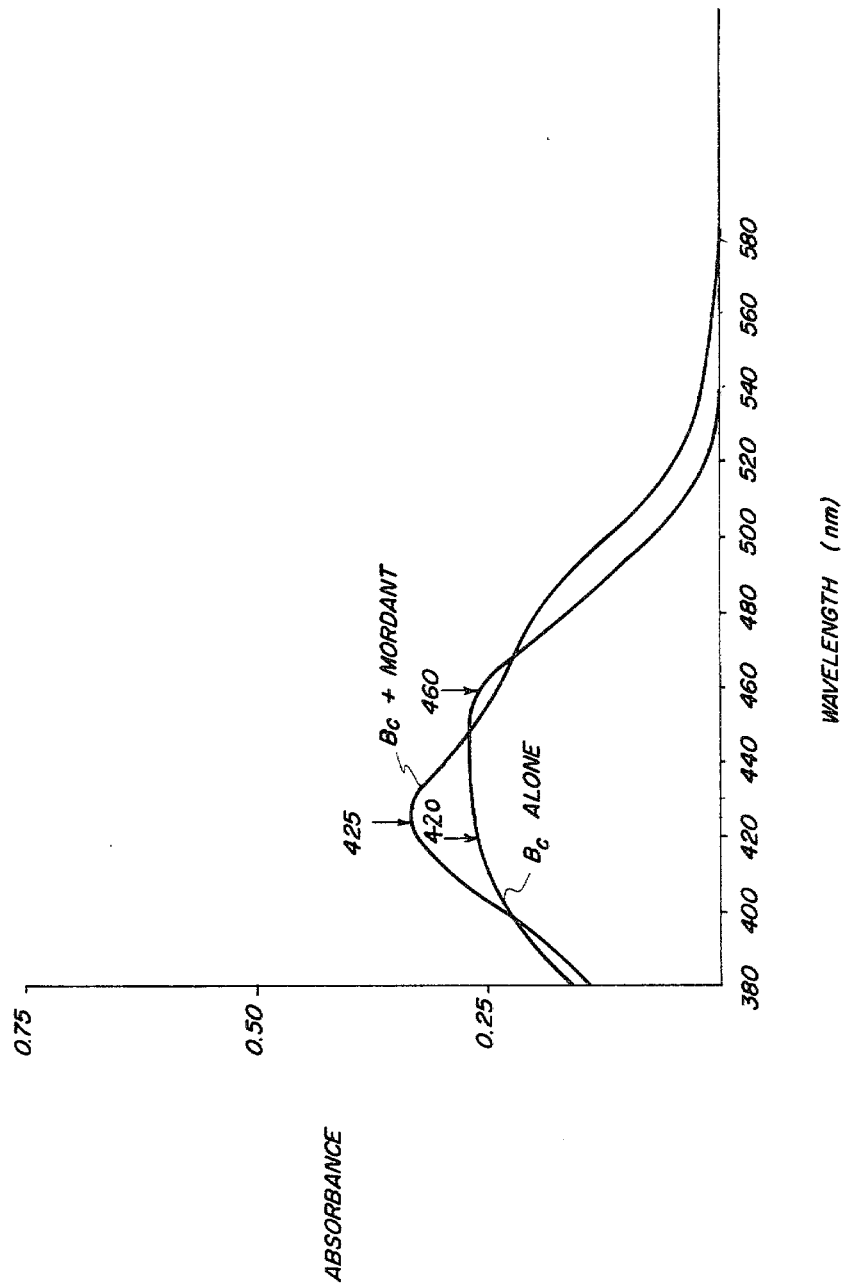
FIGS. 1 and 2 represent typical absorption spectra for $B_c$ and $B_u$ as well as mordanted $B_c$ and $B_u$.

As mentioned above, the lack of information as to $B_c$ has been found to lead to a serious source of assay error in conventional radiometric bilirubin assays. Specifically, as shown in attached FIGS. 1 and 2, the absorption spectrum of $B_u$, whether mordanted or unmordanted, has been found to exhibit significant overlap with the absorption spectrum of mordanted or unmordanted $B_c$. Accordingly, when, for example, the absorption maximum of $B_u$ at 435–440 nm is detected, a spectral absorption component of $B_c$ is also being detected and must be properly accounted for, otherwise the assay will be in error. To properly account for the $B_c$ spectral absorption component, for example, at 435–440 nm, one must have information regarding the molecular weight and molar absorption characteristics of $B_c$ at this wavelength.

The need for information regarding $B_c$ can be demonstrated as follows for the case of direct radiometric assays based on an absorption detection mode, e.g., colorimetric assays: That is, as set forth in the "Background of The Invention", typical colorimetric assays are based on Beer's law. In the case of bilirubin-containing aqueous liquids including both $B_c$ and $B_u$, the total detected absorbance, $A_T$, at a given wavelength, $\lambda$, necessarily includes the contribution of each of $B_u$ and $B_c$. Thus, $$A_T \text{ at } \lambda_1 = A_{\lambda_1} \text{ (due to } B_u\text{)} + A_{\lambda_1} \text{ (due to } B_c\text{)} \quad \text{IV}$$

which can be rewritten in accordance with Beer's Law as $$A_T \text{ at } \lambda_1 = \epsilon_{B_u}^{\lambda_1} \cdot C_{B_u} \cdot L + \epsilon_{B_c}^{\lambda_1} \cdot C_{B_c} \cdot L \quad \text{V}$$

Because L, the pathlength, is common to all aqueous liquids in a given measuring device, $$\epsilon_{B_u}^{\lambda_1} \cdot L = K_{B_u}^{\lambda_1} = \text{constant, and} \quad \text{VI}$$

$$\epsilon_{B_c}^{\lambda_1} \cdot L = K_{B_c}^{\lambda_1} = \text{constant.} \quad \text{VII}$$

Thus, equation V can be rewritten as $$A_T \text{ at } \lambda_1 = K_{B_u}^{\lambda_1} \cdot C_{B_u} + K_{B_c}^{\lambda_1} \cdot C_{B_c} \quad \text{VIII}$$

Because equation VIII contains two unknowns, namely $C_{B_u}$ and $C_{B_c}$, to determine these unknowns for a given aqueous liquid, one must necessarily detect $A_T$ at two different wavelengths, $\lambda_1$ and $\lambda_2$, thereby providing two simultaneous equations as follows:

$$A_T \text{ at } \lambda_1 = K_{B_u}^{\lambda_1} \cdot C_{B_u} + K_{B_c}^{\lambda_1} \cdot C_{B_c} \quad \text{IX}$$

$$A_T \text{ at } \lambda_2 = K_{B_u}^{\lambda_2} \cdot C_{B_u} + K_{B_c}^{\lambda_2} \cdot C_{B_c} \quad \text{X}$$

To solve equation IX and X to obtain the concentrations of $C_{B_u}$ and $C_{B_c}$, one must necessarily predetermine the molar absorption characteristics $$K_{B_u}^{\lambda_1}, K_{B_c}^{\lambda_1}, K_{B_u}^{\lambda_2} \text{ and } K_{B_c}^{\lambda_2}$$

for each of $B_u$ and $B_c$. Thereafter, equations IX and X can readily be evaluated for exact concentrations of $C_{B_u}$ and $C_{B_c}$ by detecting $A_T$ at two different wavelengths. Once the molar concentration $C_{B_u}$ and $C_{B_c}$ are evaluated, the absolute (weight) concentration of $B_u$ and $B_c$ in the aqueous liquid can be evaluated by employing the molecular weight of $B_u$ and $B_c$ as follows:

$$B_u = C_{B_u} \cdot \text{Mol Wt}_{B_u} \cdot \text{Vol. of Liquid} \quad \text{XI}$$

$$B_c = C_{B_c} \cdot \text{Mol Wt}_{B_c} \cdot \text{Vol. of Liquid} \quad \text{XII}$$

To reiterate from above, in order to solve for $C_{B_u}$ or $C_{B_c}$ in equations IX and X, the respective molar absorption characteristics for each component at each wavelength must be predetermined. The molar absorption characteristics, i.e., $$K_{B_u}^{\lambda_1}, K_{B_c}^{\lambda_1}, K_{B_u}^{\lambda_2} \text{ and } K_{B_c}^{\lambda_2},$$

are derived by establishing calibrated solutions containing known molar concentrations of $B_u$ or $B_c$. The absorbance of these calibrated solutions is measured at both $\lambda_1$ and $\lambda_2$ for various concentrations of each component and plotted against concentration. The K values for the components at $\lambda_1$ and $\lambda_2$ correspond to the slope of the absorbance/concentration plot for the components.

Although the use of a multiple wavelength approach in determining multiple analytes using a Beer's law derivation is not generally new, its extension to an assay for $B_u$ and $B_c$ has heretofore been impossible because pure $B_c$ has not been isolated and characterized as to molecular weight. Accordingly, calibrator solutions of $B_c$ were unavailable to facilitate determination of $K_{B_c}$ values. As a result of work conducted by the present inventor, a pure diconjugate species of $B_c$ having a molecular weight of 918.2 was isolated thus facilitating for the first time the formation of an appropriate calibrated solution of $B_c$. Since that time, a second, diconjugate species of $B_c$ was determined to exist having a molecular weight of 936. As set forth above the present inventor has also determined that a monoconjugate $B_c$ exists having a molecular weight as low as about 750.

Thus, $B_c$ exists as a composite of all its species. As far as can be currently ascertained, the $B_c$ species exhibit the same absorption characteristics so that a calibrator composed of one of the species will establish appropriate K values at various wavelengths that will apply to the composite bilirubin. Depending on which $B_c$ species is employed as a calibrator, therefore, a $B_c$ molecular weight in the range from about 750 to about 940 is corresponding employed to establish the molar concentration of the calibrator at each calibrator level. Similarly, in the determination of the absolute concentration of $B_c$ in a sample containing $B_c$ in unknown amounts (equivalent XII), a $B_c$ molecular weight in the same range is employed. In the latter case, collateral clinical information as to the distribution of $B_c$ species in the total $B_c$ is employed to establish a $B_c$ molecular weight in the above range that corresponds to the distribution of components. For example, in certain liver diseases such as hepatitis, liver cirrhosis, or obstructive jaundice, the diconjugate species is believed to be elevated in early stages of disease. In those circumstances, the higher end of the $B_c$ molecular weight range is preferably employed. If other tests indicate a later stage of disease is involved, a molecular weight in the middle or lower end of the $B_c$ range is employed. Accordingly, basing the assay on a $B_c$ molecular weight range from about 750 to about 940 will yield results that are more consistent with actual $B_c$ levels in samples than the results obtained by prior art methods.

In light of the foregoing discussion, it will be appreciated that the assay method of the present invention can readily be carried out by radiometrically detecting the absorption spectra of an aqueous liquid at two different wavelengths, provided the respective molar absorption characteristics of $B_u$ and $B_c$ are predetermined at these wavelengths.

The pH and temperature conditions under which the present assay can be carried out can vary considerably. In certain preferred embodiments, the assay is carried out at a pH range of from about 6.8 to about 9.5, preferably about 6.8 to about 7.6, and at a temperature within the range of from about 15° to about 60° C., preferably from about 22° to about 50° C. However, one can vary the aforementioned pH and temperature to values above or below the stated ranges depending upon the particular mordant selected, provided of course, that one does not use a pH or temperature that causes undesired side reactions or significant degradation of bilirubin.

To aid in maintaining the pH within the stated range of from about 6.8 to about 9.5, the bilirubin determination can be carried out in the presence of buffer. Various buffers can be used such as those described by Good in *Biochemistry,* 5, 467 (1966). Particularly good results have been obtained using phosphate buffers, such as potassium phosphate.

In the method of the invention, bilirubin "effectors" or "promoters", as they are sometimes called, can be added during the assay. Such "effectors" or "promoters", as noted by Henry et al in *Clinical Chemistry, Principles and Techniques* at pages 1047 and 1048 referred to in the "Background of the Invention" of this specification, are known for use in bilirubin assays. A partial listing of representative effectors includes caffeine, sodium benzoate, gum arabic, salicylate, and bile salts. The precise mechanism of these effectors is not fully understood although they may serve as solubilizing agents for the various bilirubin components. In any case, a combination of caffeine and sodium benzoate has been found especially useful in the present invention.

According to the present method, the aqueous liquid containing $B_u$ and $B_c$ is contacted together under the aforementioned pH and temperature conditions with an analytical element having an essentially dry reagent zone comprising an interactive mordant to mordant the $B_c$ and $B_u$, and the absorption or emission spectrum of the liquid containing these two different mordanted bilirubin components is detected at at least two wavelengths. The spectrum detected at each wavelength is actually a "composite" spectrum representing the sum of the individual mordanted $B_u$ and mordanted $B_c$ spectra as discussed above. In this regard it has been discovered that the molar absorptivity of mordanted $B_u$ and $B_c$ are significantly enhanced, the absorption maximum of mordanted $B_u$ is shifted, and fluorescence emission of mordanted $B_u$ and mordanted $B_c$ is produced, thereby facilitating the selective detection of these two bilirubin components.

The radiometric detection of the absorption or emission bands characteristic of the mordanted bilirubin components can be carried out by any of a variety of well-known absorption or emission detection devices and techniques. The detection of these spectral bands can be carried out at a predetermined time after the aqueous sample and interactive mordant are brought into contact so that the resultant spectral data can readily be correlated to, for example, a calibration curve based on the spectral data obtained from a series of aqueous liquid controls containing known amounts of $B_u$ and $B_c$ as determined at the same or a related predetermined time interval.

The absorption and emission bands of the mordanted bilirubin components can vary somewhat depending upon the specific interactive mordant selected. In an absorption detection mode of the invention employing preferred interactive mordant copolymers, as described in detail hereinafter and in FIGS. 1 and 2, the following spectral absorption bands can be used to selectively detect for the presence of mordanted $B_u$ and $B_c$ components: An absorption maximum corresponding to the mordanted $B_c$ (using preferred mordants) typically occurs at or about 420–430 nm, while unmordanted $B_c$ exhibits a broad absorption maximum from about 420 to 460 nm. Unmordanted $B_u$ in the presence of an aqueous liquid at a pH of about 7.4 and a temperature of about 37° C. typically exhibits a broad absorption band extending from about 400 to 470 nm with maximum absorption at or near 435 to 440 nm. An absorption maximum corresponding to the mordanted $B_u$ (again using preferred mordants) is typically shifted by at least 10 nm from that of the unmordanted form of $B_u$. Thus, the absorption maximum corresponding to the mordanted $B_u$ occurs at or beyond 445 nm, usually at or near 460 nm. To avoid spectral interference from potential interferents which may be present in the aqueous sample, e.g., hemoglobin in the case of serum samples, any of the above-noted absorption maxima can be detected off-peak. Such off-peak detection can generally be carried out at wavelengths up to 20 nm from the above-stated values. Thus, as used herein, detecting at a wavelength "at or near" an absorption maximum signifies at the peak wavelength ±20 nm and at an intensity no less than 50% of peak intensity.

In the aforementioned absorption detection mode, the molar extinction coefficients of $B_u$ and $B_c$, upon mordanting, can exhibit at least a 50 percent increase in comparison to the molar extinction coefficient of the same components unmordanted, as measured at the absorption peak of the mordanted component. Thus, as noted above, use of the interactive mordants in the present invention provides a significant enhancement of the absorption maxima of bilirubin, thereby increasing the sensitivity of the assay.

In the emission detection mode, following the contacting together of the liquid sample and the interactive mordant to mordant bilirubin, the mordanted bilirubin is subjected to activating radiation effective to excite and produce fluorescence emission of the mordanted bilirubin. Activating radiation effective to produce such fluorescence can vary somewhat depending upon the particular interactive mordant selected for use. In general, useful activating radiation effective to excite the mordanted $B_u$ and mordanted $B_c$ corresponds to the characteristic absorption wavelengths of these unmordanted bilirubin components. In a preferred embodiment, excitation radiation at the absorption wavelength of $B_c$ has been found effective to produce fluorescence emission of the mordanted $B_c$ at a wavelength within the range of from about 506–520 nm; and excitation radiation at the absorption wavelength of $B_u$ has been found effective to produce fluorescence emission of the mordanted $B_u$ at a wavelength within the range of from about 500–510 nm. The peak wavelength of the fluorescence emission of mordanted $B_c$ or $B_u$ may also vary somewhat from the ranges noted hereinabove, depending upon the particular interactive mordant selected.

Knowing the fluorescence excitation and emission wavelengths of the mordanted $B_c$ and $B_u$, one can determine the concentration of $B_c$ and/or $B_u$ present in an unknown bilirubin-containing sample in a manner analogous to that described above for the absorption detection mode. That is, one can excite a sample containing an unknown mixture of mordanted $B_c$ and mordanted $B_u$ at the excitation wavelength of $B_c$ and detect the fluorescence emission of mordanted $B_c$ at 506–520 nm, and then excite the same sample at the excitation wavelength of $B_u$ and measure the fluorescence emission of mordanted $B_u$ at 500–510 nm. The measured fluorescence emission, for example, relative fluorescence intensity values, can be converted to percent absorptance (fluorescence intensity being proportional to percent absorptance); and percent absorptance values can, in turn, be converted to absorbance values (percent absorptance being a function of absorbance). Once absorbance values are determined at two wavelengths from the fluorescence intensities measured at the fluorescence emission maxima of mordanted $B_c$ and that of mordanted $B_u$, the absolute concentration(s) of $B_c$ and/or $B_u$ in the unknown mixture is obtained through use of simultaneous equations IX and X above.

The fluorescence emission characteristics of the product formed by $B_u$ or $B_c$ and the mordants appear to be formed solely by this product. Neither $B_c$ nor $B_u$ alone, nor the mordants alone, exhibit fluorescence emission in the 480 to 520 nm range when subjected to appropriate excitation radiation.

The interactive mordants employed in the method of the invention correspond to the mordants for bilirubin described in the aforementioned U.S. Pat. No. 4,069,017. In general, these mordants have multiple binding sites for bilirubin and comprise at least one moiety having a hydrophobic organic matrix and a charge-bearing cationic group. Such mordants can be monomeric or polymeric, with especially preferred embodiments of such mordants represented by homopolymers or copolymers containing repeating units having the above-defined properties. Materials having these properties and compositions bind both $B_c$ and $B_u$ and therefore these materials function as mordants for these bilirubin components. The charge-bearing cationic group present in the mordant typically retains its cationic charge in an aqueous environment regardless of pH fluctuations. The charge properties of the cationic group in the interactive mordant are therefore insensitive to variations in pH.

Especially preferred polymeric interactive mordants have in their polymer chain monomeric units of Formula XIII below:

XIII wherein

A represents an organo group and constitutes a portion of a polymer backbone;

$n$ is 0 or 1;

O represents group linking $M^\oplus$ to A;

$M^\oplus$ represents a hydrophobic organic moiety containing a cation, preferably a quaternary ammonium or phosphonium group; and $X^\ominus$ represents an acid anion such as a halide ion, for example, chloride or bromide; nitrate; methosulfate or p-toluenesulfonate.

In certain especially useful embodiments, $M^\oplus$ represents a quaternary ammonium or phosphonium group having Formulas XIV or XV below:

XIV

XV wherein each of $R^1$, $R^2$, and $R^3$, which may be the same or different, represent an aryl, an aralkyl, or an alkaryl group preferably having from about 5 to 20 carbon atoms or an alkyl group preferably having from 1 to about 10 carbon atoms, more preferably 4 to about 10 carbon atoms.

Preferably, Q, in Formula XIII represents a hydrocarbon group, preferably an arylene, arylenealkylene, alkylenearylene, arylenebisalkylene, or alkylenebisarylene group. Preferably, O contains from about 5 to 10 carbon atoms.

As will be appreciated, A in Formula XIII above will vary depending upon the particular polymeric backbone selected for use. Especially good results, however, have been obtained when A represents an alkylene group. Typically, such alkylene groups contain from about 2 to 10 carbon atoms. Copolymers particularly useful as interactive mordants include copolymers containing about 10 to 90 wt percent of repeating units having Formula XIII hereinabove, and, in addition, up to about 75 weight percent of additional non-interfering repeating units. The term "non-interfering repeating units" is used herein to include units which do not chemically or physically interfere with the above-described mordanting of bilirubin. Monomers that provide such non-interfering repeating units and that also impart hydrophobicity to the resultant mordant copolymer include aliphatic and aromatic hydrocarbons, such as olefins and substituted olefins; styrene, and substituted styrenes; alkylacrylates and methacrylates and derivatives thereof; and known equivalents for such monomers. In addition, if desired, difunctional crosslinking groups can be introduced into such copolymers to provide crosslinked copolymers useful as interactive mordants within the scope of the present invention.

A partial listing of individual representative interactive mordants useful in the method of the invention include the following materials. (In the copolymers, the weight ratio of the two monomers entering into the polymerization reaction is 50:50, except for Polymer 6 where it is 49.5:49.5:1):

| Name | Structure |
| --- | --- |
| 1. Poly(N,N,N-trimethyl-N-vinyl-benzylammonium chloride) | 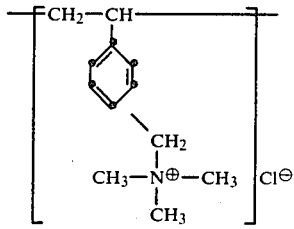 |
| 2. Poly[styrene-co-benzyl(dimethyl)-p-vinyl-benzyl-ammonium chloride] | 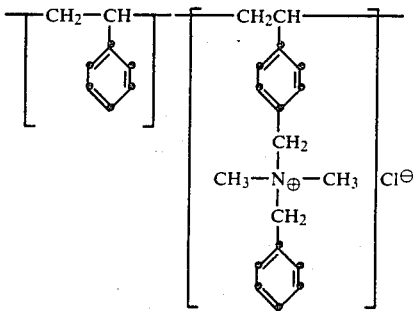 |
| 3. Poly(N,N,N-trioctyl-N-vinyl-benzylphosphonium chloride) | 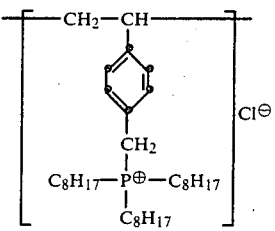 |
| 4. Poly[styrene-co-(vinyl-benzyl)-trihexyl)-ammonium chloride | 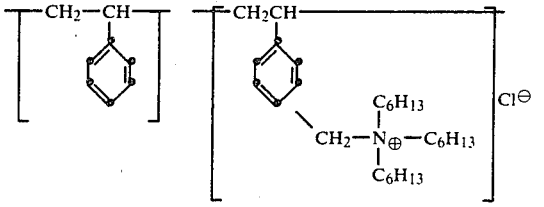 |
| 5. Poly(N,N,N-trimethyl-N-vinyl-benzylammonium chloride-co-styrene) | 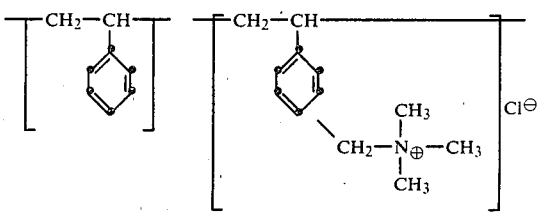 |

| Name | Structure |
|---|---|
| 6. Poly(styrene-co-N-vinyl-benzyl-N-benzyl-N,N-dimethylammonium chloride-co-divinylbenzene) | 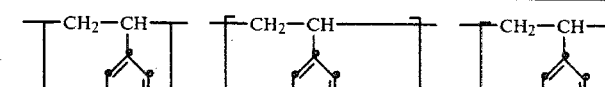 |

Further extended description of such interactive mordants including methods of preparing such compositions can be found by reference to U.S. Pat. No. 4,069,017 hereby incorporated by reference.

The amount of the above-described interactive mordants required in this method of bilirubin analysis can vary. Typically, in any given case, the amount of such interactive mordant will depend upon the particular range of bilirubin content, i.e., the "dynamic range", over which a specific bilirubin assay is designed to be useful. In preferred embodiments wherein 1 mole of bilirubin is bound or mordanted to an interactive mordant containing 1 molar equivalent amount of binding site for bilirubin, there should be sufficient interactive mordant to provide at least one molar equivalent of binding site for the maximum number of moles of bilirubin for which that assay is intended.

The amount of the mordant required will depend upon the average number of binding sites for bilirubin in the mordant and, as noted above, the dynamic range over which a specific bilirubin assay which employs such polymeric mordant is designed to be useful. In a preferred embodiment wherein a polymeric mordant, such as any one of polymeric mordants 1–6 listed above, is employed and wherein such polymeric mordant is prepared from an intermediate copolymer of styrene and vinylbenzyl chloride having an inherent viscosity (as measured at 25° C. in benzene at a concentration of 0.25 g/dl) of about 0.15 to 0.1, one can employ an amount within the range of from about 0.01 to about 1.0 g/dl of mordant to provide a assay having a dynamic range of about 0.1 to 50 mg/dl of bilirubin analyte.

In general, it is useful to employ an excess amount of interactive mordant in the bilirubin analysis method so that one can accelerate the interaction.

Dry-Chemistry Bilirubin Determination

The selective analysis of $B_u$ and $B_c$ in accord with the present invention is practiced with a "dry chemistry" analytical element which offers handling ease and overall convenience features as well as the capability of providing quantitative analytical results. Such an element comprises an essentially dry (i.e., dry-to-the-touch) reagent zone permeable to bilirubin and containing the interactive mordant. An essentially dry spreading zone and/or additional zones can also be present in the analytical elements. A preferred element comprises at least two distinct zones that are in "fluid contact" with one another under conditions of use. Fluid contact has reference to the ability of a liquid to pass between distinct zones of an element, even though the zones may be separated by intervening zones or initially spaced apart. Other zones that can be present in the element, if desired, include radiation-blocking zones, subbing zones, and the like.

Radiation-blocking zones are especially preferred for use in the present element and are interposed between the reagent zone and spreading zone to reduce optical interference from other serum components such as hemoglobin and derivatives thereof. Thus, treatment of serum samples to pre-remove spectral interferants such as hemoglobin is unnecessary. Such radiation-blocking zones include a variety of pigments, such as $TiO_2$ that mask the spectral effects of interferents. The zones also comprise a matrix for the pigment such as gelatin that maintains fluid contact between the spreading and reagent zones. Further description of radiation-blocking zones and the term "fluid contact" can be found in U.S. Pat. No. 4,069,017.

Preferably, although not necessarily, the various zones are present in an element as superposed, contiguous layers. These layers can be carried on a support, preferably a radiation transmissive support. Although preferred analytical elements are composed of superposed, contiguous layers, other elements can be prepared and employed in the method of the invention having different structural arrangements such as the use of an element having two adjacent abutting zones, namely a spreading zone and a reagent zone, both carried on a support, if necessary or desired. Such an element is illustrated, for example, in FIG. 2 of the aforementioned U.S. Pat. No. 4,069,017. For convenience and for illustrating the best mode of the invention, the dry chemistry elements employed in the invention will hereinafter be described in terms a multilayer, integral analytical element wherein the different zones are present as superposed, contiguous layers carried on a radiation-transmissive support.

In one preferred embodiment, an integral analytical element employed in the practice of this invention comprises a radiation-transmissive support having thereon, (1) a reagent layer that is permeable to at least bilirubin and that contains an interactive mordant for bilirubin, and (2) a spreading layer that is permeable to bilirubin. The reagent layer is interposed between the support and the spreading layer. The spreading layer is preferably of substantially uniform permeability to bilirubin. Preferably, the reagent layer is substantially impermeable to protein materials having a molecular weight substantially greater than that of bilirubin, e.g., albumin and other proteins having a molecular weight in the region of 60,000 (dalton units) or higher.

In a further aspect of the foregoing preferred embodiment, the spreading layer is non-fibrous and desirably isotropically porous. More preferably, all layers in the element are non-fibrous, to enhance quantitative analytical capability of the element. The term "non-fibrous" is used herein with respect to layers and/or materials to indicate that such layers or materials do not include fibrous components to a degree that would interfere with sample spreading or with detection of the analytical result by radiometric means.

Useful spreading layers can be prepared using a variety of both fibrous and non-fibrous components. Especially preferred spreading layers containing non-fibrous components are more fully described in U.S. Pat. No. 3,992,158, issued Nov. 16, 1976. In one aspect such non-fibrous spreading layers are prepared from particulate material, all desirably chemically inert to sample components under analysis. Particulate materials such as pigments, diatomaceous earth, microcrystalline colloidal materials derived from natural or synthetic polymers, e.g., microcrystalline cellulose, glass or resinous beads, and the like, can advantageously be employed in such particulate spreading layers as described in U.S. Pat. No. 3,992,158. As an alternative or an addition to such particulate material, these preferred non-fibrous spreading layer compositions can be prepared using porous polymer compositions such as "blush" polymer compositions, as also described in detail in U.S. Pat. No. 3,992,158.

The thickness of the spreading layer is variable and will depend in part on the intended sample volume, which for convenience and cleanliness the spreading layer should be able to absorb, and on the void volume of the layer, which also affects the amount of sample that can be absorbed into the lyer. Spreading layers in the range of from about 60 microns to about 300 microns dry thickness have been found particularly useful. However, thicknesses outside this range are acceptable and may be desirable for particular elements.

Reagent layers employed in the dry chemistry elements include a matrix permeable to bilirubin in which the interactive, mordant is dissolved or dispersed. However, because many of the interactive mordants are polymeric and may themselves be film-forming or otherwise readily coatable as a uniform layer or zone, a separate matrix material is not always required. The choice of a matrix material is, of course, variable and dependent on the components such as optional mordant and buffer distributed therein. In any case, any matrix material should be "non-interfering" with respect to the mordant contained therein, i.e., the matrix should be incapable of itself binding or mordanting to the interactive mordant. Further detail regarding reagent layers useful herein can be found by reference to U.S. Pat. No. 4,069,017.

One can include in the "dry chemistry" analytical element an appropriate buffer. The buffer can be incorporated in the reagent layer or in one or more of the other layers in an amount effective to impart to the reagent layer, under conditions of use of the element, a pH in the range of about 6.8 to about 9.5.

In preparing the integral analytical elements, the layers can be preformed as separate layers that are laminated together prior to use or maintained as separate layers until brought into fluid contact when the element is in use. Detailed description of techniques for the preparation of these dry chemistry test element can be found by reference to U.S. Pat. Nos. 3,992,158 and 4,069,017 noted above.

As mentioned previously herein, the present analytical elements can be self-supporting or carried on a support. Useful support materials include a variety of polymeric materials such as cellulose acetate, poly(ethylene terephthalate), polycarbonates and polyvinyl compounds such as polystyrenes, etc. A support of choice for any particular element will be compatible with the intended mode of result detection. Preferred supports include radiation-transmissive support materials that transmit electromagnetic radiation of a wavelength or wavelengths within the region between about 300 nm and about 700 nm. It may also be desirable to have a support that transmits one or more narrow wavelength bands and is opaque to adjacent wavelength bands. This could be accomplished, for example, by impregnating or coating the support with one or more colorants having suitable absorption characteristics.

In the layers of the element, it can be advantageous to incorporate one or more surfactant, for example, anionic and nonionic surfactants. They can, for example, enhance coatability of layer formulations and enhance the extent and rate of spreading in spreading layers that are not easily wetted by liquid samples. In particular, it can be desirable to incorporate a relatively large amount of a surfactant, such as a nonionic surfactant, in the spreading layer to normalize transport of bilirubin contained in an aqueous proteinaceous liquid sample in and through this layer. Such normalization refers to obtaining within the spreading layer an equivalent penetration of the solvent medium and bilirubin contained in various applied samples of aqueous proteinaceous liquids, notwithstanding variations in protein concentration among such samples. In addition, it has been found that because bilirubin is often present in a "bound-state" such as bound to other proteins, e.g., serum albumin, the use of such surfactants in the spreading layer to achieve normalization of bilirubin transport advantageously appears to dissociate bilirubin bound to such protein. Preferred amounts of surfactant effective to achieve normalized bilirubin transport are typically between about 1% and about 15% by weight based on the dry weight of the layer. Further details regarding this use of surfactants to achieve normalized analyte transport may be found by reference to Goffe, Rand, and Wu, U.S. Pat. No. 4,050,898, issued Sept. 27, 1977.

Other interlayers may also be present in integral analytical elements employed as dry chemistry test elements. For instance, a separate interlayer swellable in the solvent or dispersion medium of the liquid sample under analysis can be used. Such a swellable interlayer, preferably radiation-transmissive, e.g., a swellable gel layer, can be incorporated between the reagent layer and support of an integral analytical element and could be used to enhance the permeation or "spread rate" of a bilirubin-containing serum sample through the spreading layer into the reagent layer of the element. As another example an interlayer can be incorporated into an analytical element of the invention between the spreading layer and the reagent layer thereof. Such a layer should, of course, be permeable to bilirubin and can be used to incorporate reagent materials that can render various interferents for bilirubin inactive or can be used to filter and thereby remove such interferents.

As can be appreciated, dry chemistry analytical elements useful in the present invention can be configured in a variety of forms, including elongated tapes of any desired width, sheets or smaller chips.

Preferred dry chemistry analytical elements are used by applying to the element a sample of liquid under analysis. The applied sample will normally contact a spreading layer prior to the reagent layer and at the spreading layer surface furthest removed from such reagent layer.

After sample application, and desirably after the liquid sample has been taken up by a spreading layer, the element is exposed to any conditioning, such as heating, humidification that may be desirable to facilitate obtaining any test result.

After the analytical result is obtained as a detectable change, it is measured, usually by passing the element through a zone in which suitable apparatus for reflection or transmission colorimetry or spectrofluorimetry is provided. In a colorimetric detection mode, such apparatus would serve to direct a beam of energy, such as light, through the support and the reagent layer. The light would then be reflected, such as from an opacifying agent in the spreading or a radiation-blocking layer in the element, back to a detecting means or would pass through the element to a detector.

In a fluorimetric detection mode, such apparatus would serve to direct a beam of light through the support and the reagent layer to excite the mordanted bilirubin in the reagent layer and stimulate fluorescent emission of light radiation by the mordanted bilirubin. This fluorescence emission would then be reflected, such as from an opacifying agent in the spreading layer of the element, back to a detecting means or would pass through the element to a detector.

Various calibration techniques can be used to provide a control for the analysis. As one example, a sample of analyte standard solution can be applied adjacent the area where the drop of sample is placed in order to permit the use of differential measurements in the analysis.

The following Examples are presented for a better understanding of the invention. The following procedures and materials were employed in the Examples:

Procedures

1. Simultaneous equations IX and X hereinabove were employed in the examples below to aid in the determination of the unknown concentrations of $B_u$ and $B_c$ in an aqueous liquid. To use these equations, the following analysis was used:

Transmission density $D_T$, was assumed to be approximately equal to absorbance, A, for the case of homogeneous thin films and solutions. Therefore, equations IX and X were rewritten as:

$$D_T \text{ at } \lambda_1 = K_{Bu}^{\lambda_1} \cdot C_{Bu} + K_{Bc}^{\lambda_1} \cdot C_{Bc} \text{ and} \qquad \text{XVI}$$

$$D_T \text{ at } \lambda_2 = K_{Bu}^{\lambda_2} \cdot C_{Bu} + K_{Bc}^{\lambda_2} \cdot C_{Bc} \qquad \text{XVII}$$

Then, using $\lambda_1 = 460$ nm and $\lambda_2 = 420$ nm, equations XVI and XVII were rewritten as:

$$D_T \text{ at } 460 = K_{Bu}^{460} \cdot C_{Bu} + K_{Bc}^{460} \cdot C_{Bc} \qquad \text{XVIII}$$

$$D_T \text{ at } 420 = K_{Bu}^{420} \cdot C_{Bu} + K_{Bc}^{420} \cdot C_{Bc} \qquad \text{XIX}$$

By algebraic substitution and transformation, equations XVIII and XIX can be rewritten as:

$$C_{Bc} = \frac{D_T \text{ at } 460 \cdot K_{Bu}^{420} - K_{Bu}^{460} \cdot D_T \text{ at } 420}{K_{Bc}^{460} \cdot K_{Bu}^{420} - K_{Bc}^{420} \cdot K_{Bu}^{460}} \qquad \text{XX}$$

$$C_{Bu} = \frac{D_T \text{ at } 420 \cdot K_{Bc}^{460} - D_T \text{ at } 460 \cdot K_{Bc}^{420}}{K_{Bc}^{460} \cdot K_{Bu}^{420} - K_{Bu}^{460} \cdot K_{Bc}^{420}} \qquad \text{XXI}$$

2. In the case of multilayer analytical elements having a reflective layer, certain of the examples reported below measured optical density values in terms of reflection density, $D_R$, rather than transmission density, $D_T$. In these cases, $D_R$ values were converted to $D_T$ values by the following transformation:

$$D_T = -0.194 + 0.469 D_R + \frac{0.422}{1 + 1.17e^{3.37 D_R}} \qquad \text{XXII}$$

The use of the above-noted transformation is applicable to the transformation of $D_R$ to $D_T$ values for the case of a thin film multilayer analytical element such as described below in Materials, and is similar to the transformation of $D_R$ to $D_T$ values discussed by Williams and Clapper, "Multiple Internal Reflections in Photographic Color Prints", *J. Opt. Soc. Am.*, Vol. 43, p. 595 (1953). The use of this transformation is also discussed in Curme et al, "Multilayer Film Elements for Clinical Analysis: General Concepts", *Clinical Chemistry*, Vol. 24, p. 1335 at 1340 (1978).

3. Aqueous solutions of $B_c$ and $B_u$ described in the examples below were prepared by the method of J. I. Routh as set forth in *Fundamentals of Clinical Chemistry*, Ed: N. W. Tietz, W. B. Saunders Company, Philadelphia, p. 1026-1031 (1976).

Materials

1. Unconjugated bilirubin ($B_u$) was purchased from Sigma Chemical Co., St. Louis, Mo. Conjugated bilirubin ($B_c$) prepared from bile was obtained by a modified Lucassen procedure (Lucassen, "The Diazo Reaction of Bilirubin and Bilirubin Diglucuronide", Doctoral Thesis, University of Utrecht, Netherlands (1961)) as described in the Wu et al paper presented at the American Association for Clinical Chemistry referenced in the Background of the Invention. Conjugated bilirubin ($B_c$) prepared from human serum was obtained using an interactive mordant as described in Example 2 of Wu, copending application Ser. No. 056,585, filed July 11, 1979, and entitled "Separation and Isolation of Conjugated and Unconjugated Bilirubin" abandoned in favor of continuation-in-part application Ser. No. 101,663 filed Dec. 10, 1979, now U.S. Pat. No. 4,311,665. This application is incorporated by reference herein. Example 2 of the aforesaid application was carried out as follows: First, a pool of serum having a high $B_c$ concentration (jaundiced sera having a total bilirubin concentration equal to or in excess of 20 mg/dl, of which 70-80% appeared as "direct" bilirubin in a Jendrassik-Grof assay) was diluted 1 to 5 (v/v) with distilled water under nitrogen. This solution was carefully titrated with mordant 4 of Table I (made up to 1% fresh in water containing 5-10% methanol) until the absorbance at 425 nm stopped increasing. With mild excess of mordant 4, the absorbance at 425 nm decreased slightly. The titrated solution appeared turbid and was rapidly centrifuged for 15 minutes at 15,000 g at 0°-4° C. The yellowish mordanted pellet was gently resuspended in 3 volumes of 0.05 to 0.1 M potassium phosphate buffer, pH 7.0, to which 1% $Na_2S_2O_3$ had been added. To the cloudy suspension was added dropwise a fresh solution of caffeine and sodium benzoate until the final level of caffeine was approximately 0.1 M and that of benzoate 0.2 M. During this time, the solution was stirred vigorously under nitrogen and in a bath of ice. The solution was allowed to stand for ½ hour in the dark and cold (0°–4° C.), then centrifuged at 10,000×g for 15 minutes. The supernatant was saved. The pellet was washed at least twice with an equal volume of 0.1 M potassium phosphate buffer, pH 7.0, then three to four times with a 1:1 (v/v) mixture of 1 M NaCl and n-propanol. The washings were pooled with the supernatant from the preceding centrifugation, then stirred under nitrogen and in the dark for ½ hour. The solution was freeze-dried; the resultant powder was resuspended in a minimal amount of water and loaded on a column containing LH-20 gel beads (purchased from Pharmacia, Uppsala, Sweden) packed with 95% ethanol diluted 1:1 (v/v) with 0.1 M potassium phosphate buffer, pH 7.0. The same solvent mixture served as the eluting medium. The yellow eluted fractions were pooled, rechromatographed on a fresh column as before, and immediately freeze-dried. The resulting brownish-yellow powder contained a concentrated diconjugate species of $B_c$ having a molecular weight of 918.2 and a purity of about 85% based on quantitative NMR (nuclear magnetic resonance) and gravimetric analysis.

2. Human sera used in the following examples were supplied by local hospitals. Serum samples, if not used immediately, were kept frozen at −25° C. in the dark. If not used in one week, the samples were not used at all. Samples were not reused after thawing.

3. The mordants used were mordants 4 or 6 of Table I.

4. The thin film multilayer analytical element used in certain of the examples below had the following structure and composition:

| | | g/m² |
|---|---|---|
| | $TiO_2$ | 50.0 |
| | cellulose acetate | 7.0 |
| Reflecting | Caffeine | 2.69 |
| Spreading | Sodium Benzoate | 4.035 |
| Layer | Octylphenoxypolyethoxy ethanol surfactant | 1.4 |
| | Polyoxyethylene oleyl ether surfactant | 0.9 |
| Subbing Layer | Poly(N-isopropylacrylamide) | 0.387 |
| | | 1.72 |
| Mordant | Deionized gelatin | 8.608 |
| Layer | N,N-bis(2-hydroxyethyl) glycine buffer, 0.2 M; pH 8.0 | 3.5 |
| Support Layer | Poly(ethylene terephthalate) | |

5. Other chemicals noted in the examples below were obtained from Eastman Organic Chemicals, Eastman Kodak Co., Rochester, N.Y. Unless otherwise specified, the chemicals used were reagent grade.

An alternative and preferred element that is used has the following structure and composition:

| | | g/m² |
|---|---|---|
| | $TiO_2$ | 60.55 |
| | Cellulose acetate | 8.42 |
| Spreading | Octylphenoxypolyethoxyethanol | 1.65 |
| Layer | Polyoxyethylene oleyl ether | 0.84 |
| | Caffeine | 6.46 |
| | Sodium benzoate | 4.85 |
| Subbing Layer | Poly(N-isopropylacrylamide) | 0.39 |
| Radiation | $TiO_2$ | 32.29 |
| Blocking | Deionized gelatin | 3.23 |
| Layer | Surfactant ® 10 G | 0.092 |
| | Mordant | 1.76 |
| Mordant | Deionized gelatin | 8.78 |
| Layer | N,N-bis(Z-hydroxyethyl)glycine buffer, 0.2M; pH 8.0 | 3.5 |
| | Gelatin hardener | 0.08 |
| Support Layer | Poly(ethylene terephthalate) | |

EXAMPLE 1

Determination of Molar Absorption Characteristics of Mordanted $B_u$ and $B_c$ in Multi-layer Element In this example two series of bilirubin solutions were prepared, one series consisting of aqueous solutions of $B_c$ (from human bile) at varying concentration levels and one series consisting of aqueous $B_u$ solutions at varying concentration levels. Each solution was then spotted onto a multilayer analytical element (as described in Materials 4 above) and the transmission density of each solution was measured at 460 nm and 420 nm using a common spectrophotometer. Plots of $D_T$ vs. molar concentration of $B_u$ using a $B_u$ molecular weight of 584 were made for the one series of solutions at 460 nm and also at 420 nm; plots of $D_T$ vs. molar concentration of $B_c$ using a $B_c$ molecular weight of 918.2 were made for the other series of solutions also at 460 nm and 420 nm. The slopes of these 4 plots were then evaluated, i.e. $\Delta D_T$ divided by Δ molar concentration, to obtain the molar absorption constant K ($K=\epsilon \cdot L$ from equation VI and VII above) for $B_c$ and $B_u$ at 460 nm and 420 nm. Estimating the pathlength, L, in each of the multilayer test elements to be approximately equal to 0.0568 mm, the molar absorptivity, ε, for mordanted $B_u$ and mordanted $B_c$ was also determined at 460 and 420 nm. The results are shown below in Table II.

TABLE II

| nm | $K_{Bu}$ mordant | $\epsilon_{Bu}$ mordant | $K_{Bc}$ mordant | $\epsilon_{Bc}$ mordant |
|---|---|---|---|---|
| 460 nm | 500 | 88,000 | 236 | 41,536 |
| 420 nm | 362 | 63,712 | 334 | 58,784 |

EXAMPLE 2

Spectral Enhancement of $B_c$ in Presence of Mordant

A freshly isolated sample of serum $B_c$ in aqueous solution at pH 7.4 was placed in a cuvette, and the absorption spectrum (300-700 nm) was recorded on a spectrophotometer. A small amount of Mordant 4 of Table I was then added to the specimen, and the absorption spectrum was again recorded. The sample alone displayed a broad spectrum with an apparent maximum in the vicinity of 420 to 460 nm, whereas, in the presence of the Mordant 4, the sample became selectively amplified at ~420-425 nm. This behavior resembled that previously observed with $B_c$ obtained from other biological sources such as human bile. Results are shown in FIG. 1.

EXAMPLE 3

Spectral Enhancement of $B_u$ in Presence of Mordant

Figure 2:
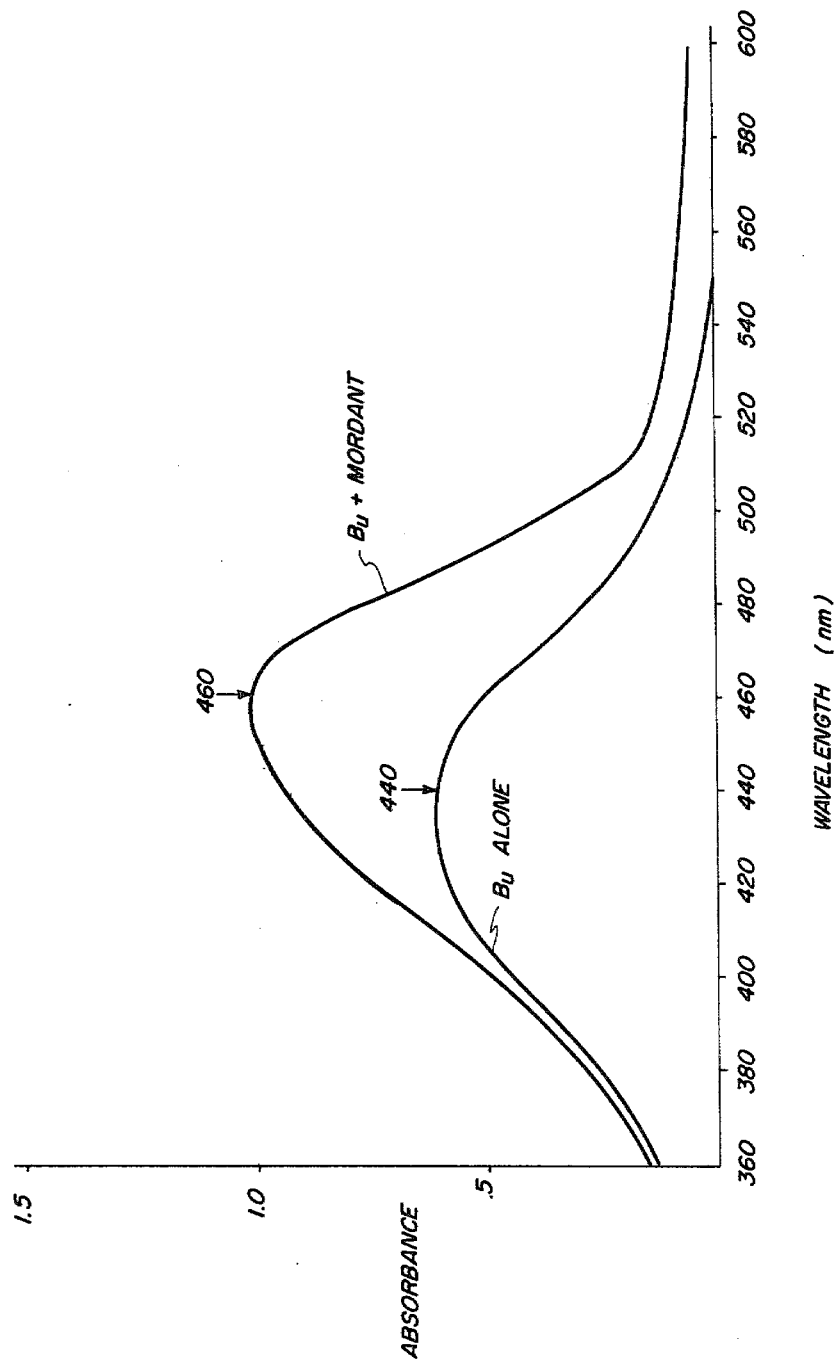

A sample of $B_u$ in aqueous solution at pH 7.4 was placed in a cuvette, and the absorption spectrum (360–600 nm) was recorded on a spectrophotometer. A small amount of Mordant 6, Table I, was then added to the specimen, and the absorption spectrum was again recorded. The sample alone displayed a broad spectrum with apparent maximum in the vicinity of 435–440 nm whereas, in the presence of Mordant 6, the sample became selectively amplified at 460 nm, accompanied by a two-fold increase in its absorption at the new peak. Results are shown in FIG. 2.

EXAMPLE 4

Quantitative Determination of $B_u$ and $B_c$ in Multilayer Analytical Element With Mordant Calibrator solutions were prepared as follows: varying amounts of $B_u$ were dissolved in aliquots of pooled human serum to obtain final $B_u$ levels (as determined gravimetrically) of approximately 1, 5, 10, and 20 mg/dl. Similarly, freshly purified $B_c$ (from human bile) was diluted with aliquots of the same serum pool to give final $B_c$ levels of approximately 1, 5, 10, and 20 mg/dl.

In addition, a third set of solutions with varying amounts of $B_u$ and $B_c$ (from human bile) was prepared in aliquots of the same serum pool.

Each solution of the third set (noted above) was spotted on a separate multilayer analytical element (each element having an identical formulation as described in Materials 4 above), incubated for 5 minutes at 37° C., after which the reflectance densities, $D_R$, were measured at 420 nm and 460 nm for each spot. The analytical elements were calibrated with the above-noted calibrator solutions to determine the constants $K_{Bu}$ and $K_{Bc}$ using a $B_c$ molecular weight of 918.2 and a $B_u$ molecular weight of 584. Reflectance density values were converted to transmission density, $D_T$, values as described in Procedure 2 above. The simultaneous equations shown in Procedure 1 above were then used to obtain the molar concentration of $B_u$ and $B_c$ in each of the third set solutions. Molar concentrations of $B_c$ and $B_u$ were converted to mg concentrations using the molecular weights 918.2 and 584 for $B_c$ and $B_u$ respectively. Results comparing gravimetric values to the values determined by the multilayer analytical element are shown in Table III. As shown in Table III, good agreement between the values determined by the multilayer analytical element using the method of the invention and the gravimetric values was obtained.

TABLE III

| Gravimetric Values mg/dl | | Measured Values (by method of invention) mg/dl | |
|---|---|---|---|
| $B_u$ | $B_c$ | $B_u$ | $B_c$ |
| 20 | 10 | 22 | 9.0 |
| 20 | 5 | 19 | 6.1 |
| 20 | 20 | 19.3 | 18 |
| 20 | 1 | 18.0 | 1.4 |
| 10 | 20 | 11.8 | 18.7 |
| 5 | 20 | 4.8 | 20.7 |
| 1 | 20 | 1.4 | 20.9 |
| 1 | 1 | 0.87 | 0.90 |
| 5 | 1 | 4.64 | 1.5 |
| 10 | 1 | 9.3 | 1.04 |

EXAMPLE 5

Comparison of Multilayer Element Method of the Present Invention With Reference Method Ten patient samples were assayed at a local hospital for total bilirubin and "direct" bilirubin according to the Jendrassik-Grof method. The samples were then assayed by the method of the invention employing the multilayer analytical element (described in materials 4 above) using the technique described in Example 4 above. $B_T$ by the method of the present invention was obtained by adding together the measured values obtained for $B_c$ based on a molecular weight of 918.2 and $B_u$ based on a molecular weight of 584. The results are shown in Table IV. As shown in Table IV, $B_T$ values from Jendrassik-Grof agree fairly closely with $B_T$ values by the present method. "Direct" values by the Jendrassik-Grof assay differ from the $B_c$ values of the present method because, among other reasons, "direct" values include some $B_u$ and because the "direct" values are calibrated with $B_u$ alone.

TABLE IV

| | Summary of Patient Data | | | |
|---|---|---|---|---|
| | Jendrassik-Grof (mg/dl) | | Method of Invention (mg/dl) | |
| Patient No. | $B_T$ | Direct Bilirubin | $B_T$ | $B_c$ |
| 1 | 6.4 | 3.8 | 6.4 | 3.6 |
| 2 | 4.0 | 3.0 | 3.76 | 2.74 |
| 3 | 5.2 | 4.2 | 5.12 | 3.8 |
| 4 | 6.0 | 4.6 | 5.29 | 3.34 |
| 5 | 6.2 | 3.8 | 6.93 | 4.24 |
| 6 | 5.2 | 3.0 | 5.59 | 3.55 |
| 7 | 14 | 10.9 | 13.16 | 9.398 |
| 8 | 17.1 | 11.9 | 17.8 | 11.8 |
| 9 | 7.5 | 5.4 | 6.6 | 3.9 |
| 10 | 21.6 | 16.0 | 23.6 | 17.2 |

What is claimed is:

1. A method for the selective determination of the unconjugated bilirubin ($B_u$) or conjugated bilirubin ($B_c$), as well as the total bilirubin ($B_T$), content of an aqueous liquid, containing $B_c$ and $B_u$, said method comprising:
  (A) contacting together said aqueous liquid with an analytical element having an essentially dry reagent zone comprising an interactive mordant for bilirubin to mordant bilirubin, the mordanted bilirubin exhibiting a detectable absorption or emission spectrum containing the individual absorption or emission bands characteristic of each of the mordanted $B_u$ and $B_c$ components in said aqueous liquid;
  (B) detecting the absorption or emission spectra of said mordanted bilirubin at two absorption or emission wavelengths thereof,
    (1) one wavelength being at or near an absorption or emission maximum of mordanted $B_u$,
    (2) one wavelength being at or near an absorption or emission maximum of mordanted $B_c$, and
    (3) the molar absorption or emission characteristics of mordanted $B_u$ and mordanted $B_c$ for each of these wavelengths having been predetermined based on a $B_u$ molecular weight of 584 and a $B_c$ molecular weight in the range from about 750 to 940; and
  (C) determining $B_u$, $B_c$ and/or $B_T$ from said absorption or emission spectra and said molar absorption or emission characteristics.

2. The method of claim 1 wherein said aqueous liquid is serum.

3. The method of claim 1 or 2 wherein the detection step is carried out spectrophotometrically.

4. The method of claim 1 or 2 wherein the aqueous liquid is brought into contact with the interactive mordant at a pH in the range of from about 6.8 to 9.5 and at a temperature within the range of from about 15° to 60° C.

5. The method of claim 1 wherein the interactive mordant is a polymeric mordant having repeating monomeric units of the formula:

XIII wherein
A represents an organo group constituting a portion of the polymer backbone;
$n$ is 0 or 1
Q represents a chemical bond(s) or a chemical group linking $M^{\oplus}$ to A;
$M^{\oplus}$ represents a hydrophobic organic moiety containing a cation, and
$X^{\ominus}$ represents an acid anion.

6. The method of claim 5 wherein the polymeric mordant is a copolymer having recurring units having Formula XIII and up to 75 weight percent of additional non-interfering repeating units.

7. The method of claim 6 wherein the $M+$ *moiety has the formula*:

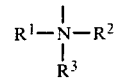

wherein
each of $R^1$, $R^2$ and $R^3$ are the same or different, and represent an alkyl, an aryl, an aralkyl, or an alkaryl group.

8. The method of claim 6 wherein the mordant is poly(N,N,N-trimethyl-N-vinyl-benzylammonium chloride), poly[styrene-co-benzyl(dimethyl)-p-vinyl-benzylammonium chloride], poly(N,N,N-trioctyl-N-vinylbenzylphosphonium chloride), poly[styrene-co-(vinylbenzyl)-(trihexyl)-ammonium chloride], poly(N,N,N-trimethyl-N-vinylbenzylammonium chloride-co-styrene) or poly(styrene-co-N-vinylbenzyl-N-benzyl-N,N-dimethyl-ammonium-chloride-co-divinylbenzene).

9. The method of claim 5 wherein the reagent zone is a reagent layer of a multilayer analytical test element containing a spreading layer, the reagent layer, and a radiation-transmissive support, the spreading layer and the reagent layer being in fluid contact with one another and being present in the element as superposed layers on said support.

10. The method of claim 9 wherein said multilayer analytical element further comprises a radiation-blocking layer interposed between and in fluid contact with said spreading layer and reagent layer.

11. The method of claim 10 wherein said radiation-blocking layer comprises titanium dioxide in an amount sufficient to reduce spectral interference from hemoglobin in said aqueous liquid.

12. The method of claim 1 wherein the absorption spectra of said mordanted bilirubin is detected.

13. The method of claim 1 wherein the emission spectra of said mordanted bilirubin is detected.

* * * * *